United States Patent [19]

Orth et al.

[11] Patent Number: 5,169,990

[45] Date of Patent: Dec. 8, 1992

[54] PREPARATION OF 9,9-BIS-(4-HYDROXYPHENYL)-FLUORENE

[75] Inventors: Winfried Orth, Hassloch/Pfalz; Emmerich Pastorek, Hemsbach a.d. Bergstrasse; Wolfgang Weiss, Neckarhausen; Hans W. Kleffner, Battenberg/Pfalz, all of Fed. Rep. of Germany

[73] Assignee: Rutgerswerke Aktiengesellschaft

[21] Appl. No.: 833,769

[22] Filed: Feb. 11, 1992

[30] Foreign Application Priority Data

Mar. 7, 1991 [DE] Fed. Rep. of Germany ....... 4107241

[51] Int. Cl.⁵ .................. C07C 39/12; C07C 37/20
[52] U.S. Cl. .................... 568/719; 568/718; 568/722; 568/727; 568/733; 568/125; 568/190
[58] Field of Search .............. 568/718, 719, 721, 733, 568/125, 190, 722, 727

[56] References Cited

U.S. PATENT DOCUMENTS

| | | |
|---|---|---|
| 3,546,165 | 12/1970 | Morgan ............................ 528/125 |
| 4,024,194 | 5/1977 | Corn, Jr. et al. .................... 568/719 |
| 4,049,722 | 9/1977 | Corn, Jr. et al. .................... 568/719 |
| 4,675,458 | 6/1987 | Riemans et al. ................... 568/719 |

FOREIGN PATENT DOCUMENTS

| | | | |
|---|---|---|---|
| 0180133 | 5/1986 | European Pat. Off. ........... 568/719 |
| 0314007 | 5/1989 | European Pat. Off. ........... 568/719 |

*Primary Examiner*—Werren B. Lone

[57] ABSTRACT

In the production of 9,9-bis-(4-hydroxphenyl)-fluorene by condensation by fluorenone and phenol in a molar ratio of 1:4 to 1:8 at 30° to 90° C. in the presence of gaseous hydrogen chloride and β-mercapto-propionic acid as catalyst, the improvement comprising mixing the completed reaction mixture with a polyalkylene glycol, distilling excess phenol from the mixture, and mixing the distillation residue with a solvent miscible with the polyalkylene glycol, recovering the crystallized product, suspending the crystallized product in water and heating the suspension to obtain highly pure 9,9-bis-(4-hydroxyphenyl)-fluorene as white crystals.

5 Claims, No Drawings

PREPARATION OF 9,9-BIS-(4-HYDROXYPHENYL)-FLUORENE

STATE OF THE ART

In the plastics industry, such bisphenols are used on a large scale in polycondensation processes, particularly as monomers. The products made from them are polyester resins and plastics with especially good heat-resistance properties which can be used for insulation of electrical conductors or for highly thermostable coatings. However, plastics with these advantageous properties can be obtained only if especially pure bisphenols are used for their production.

In accordance with the economic importance, therefore, numerous attempts at improving known synthesis methods and purifying the reaction products have been made. Playing a central role in this connection is the process described by Morgan (Morgan, Macromolecules, Vol. 3,P536 (1970) and U.S. Pat. No. 3,546,165), by which nearly all later processes were inspired. According to Morgan, fluorenone and phenol are used in the condensation reaction in a molar ratio of 1 : 4, so that the phenol functions during the reaction both as reagent and as solvent. The reaction itself proceeds in the presence of $\beta$-mercaptopropionic acid or mercaptoacetic acid with introduction of dry HCl gas at a temperature between 140 and 150° C. The high temperatures are necessary at this mixture ratio of the reagents so that the composition will remain stirrable. But, as later experiments have shown, they lead to the formation of undesired by-products.

The dilution with water or the steam distillation proposed by Morgan after the condensation reaction is unsuitable for processing the reaction mixture on an industrial scale. Although upon dilution with water, a white compound actually forms, it is compact, sticky, and no longer manageable in larger quantities. By steam distillation, too, the same sticky compound is obtained. Besides, evidently an additional discoloration of the reaction product is brought about by the treatment with hot water, and crystallization of the product is prevented.

According to Morgan's description, the separated product is dissolved in an alkaline solution and then precipitated by dropwise addition of hydrochloric acid. After crystallization from toluene, 9,9-bis-(4-hydroxphenyl)-fluorene is obtained as a white crystalline product having a melting point of 224 to 225° C. in a yield of 46 to 56% of the theory. However, applicants' attempts to dissolve the above described white compound in alkaline solution proved costly and lengthy.

Later processes, therefore, aimed to increase the yield, and to simplify the processing. In the course of time, a variety of catalysts usable in the process were tried to increase the yield. They included ionizable sulfur compounds such as e.g. sulfur monochloride, hydrogen sulfide, a variety of mercapto compounds or alkali metal sulfides which react with acids with formation of hydrogen sulfide. Also Friedel-Crafts catalysts were used, as e.g. $ZnCl_2$, $CaCl_2$, $AlCl_3$ or $SnCl_4$, which are active in the presence of HCl.

It was found, however, that not only the choice of catalyst has a determining effect on the yield and on the product quality, but so does particularly the reaction temperature and the molar ratio of the reagents. High yields could therefore be achieved both with Friedel-Crafts catalysts and with the mercaptopropionic acid described by Morgan if the reaction temperature was kept below 100° C., more particularly between 30 and 90° C., and if phenol was used in a 4 to 8 molar quantity based on the fluorenone.

In this temperature range is carried out also the condensation reaction in the process described in document DE-OS 34 39 484. Fluorenone and phenol are reacted in a molar ratio of 1 : 4 to 1 : 6 in the presence of $\beta$-mercaptopropionic acid and concentrated sulfuric acid. By the subsequent workup, a crude yield of about 97 to 98% is obtained according to the reference. This, however, still includes a high proportion of undesired by-products, formed by dimerization and substitution. The further processing occurs in that, after the completed condensation reaction, methanol is added and only then is the mixture poured into cold water whereby an oily compound separates. The supernatant, aqueous methanol-sulfuric acid-phenol solution, is separated and the residue is washed twice with water and neutralized with ammonium carbonate solution. Phenol still adhering is removed by repeated boiling with water. After drying and a second crystallization from isopropyl alcohol, a product having a melting point of 223° C. is obtained.

This process, however, has major disadvantages. In the processing of the reaction product, very large amounts of water contaminated with phenol and sulfuric acid occur which must be given special treatment under the clean water regulations. Besides, the lumpy crude product obtained in this process after the addition of water is difficult to handle as it filters poorly and is difficult to wash and neutralize for further purification.

OBJECTS OF THE INVENTION

It is an object of the invention to provide an inexpensive, easily performable process for the production of 9,9-bis-(4-hydroxyphenyl)-fluorene in high yield and purity which makes it possible to separate in a simple manner the solvents used for product purification so that, if desired, they can be re-used in the process.

This and other objects and advantages of the invention will become obvious from the following detailed description.

THE INVENTION

The novel process of the invention for the preparation of 9,9-bis-(4-hydroxphenyl)-fluorene by condensation by fluorenone and phenol in a molar ratio of 1:4 to 1:8 at 30 to 90° C. in the presence of gaseous hydrogen chloride and $\beta$-mercapto-propionic acid as catalyst, the improvement comprises mixing the completed reaction mixture with a polyalkylene glycol, distilling excess phenol from the mixture, and mixing the distillation residue with a solvent miscible with the polyalkylene glycol, recovering the crystallized product, suspending the crystallized product in water and heating the suspension to obtain highly pure 9,9-bis-(4-hydroxyphenyl)-fluorene as white crystals.

It has been found that the hydrochloric acid contained in the reaction mixture can be easily distilled off together with the resulting reaction water under reduced pressure if the method of Morgan is followed which has the advantage that one can work under much milder conditions with fewer undesirable by-products due to dimerization and substitution formed when working with concentrated sulfuric acid. At the same time, the disadvantages can thereby be avoided which occur in the product processing and through the then occurring solvent quantities when working in the presence of sulfuric acid or of Friedel-Crafts catalysts.

The condensation reaction of fluorenone and phenol in the presence of gaseous hydrogen chloride proceeds with sufficient speed already at 30° C. Preferably one operates at temperatures between 50 and 60° C. as in this range, there is little formation of by-products and the reaction time to complete reaction of fluorenone is acceptably short. If, as indicated in Morgan, the reagents, fluorenone and phenol, are used in a molar ratio of 1 : 4, the substance solidified toward the end. But if phenol is used in 6 to 8 times the molar quantity, based on fluorenone, the composition remains stirrable throughout.

After the reaction, it is possible to remove the reaction water jointly with dissolved hydrochloric acid by distillation under reduced pressure, but if the phenol is used in excess, this is not advisable. If it is distilled off completely, a compact mass as distillation residue is obtained, which can no longer be processed further. It has now been found, surprisingly, that this can be avoided by addition of a small amount of a polyalkylene glycol. The distillation residue remains thin and stirrable and is crystallized out of a solvent miscible with this glycol such as dichloroethane, toluene, ether, or nitromethane in a manner known in itself.

With the process according to the invention, it is possible to distill phenol used in excess for the reaction out of the reaction mixture and to return it to the process again. As it is possible to remove the hydrochloric acid contained in the reaction mixture together with the reaction water, before the removal of the phenol by distillation, the otherwise customary washing with water and steam distillation are obviated.

Another advantage is seen in that the crystallization can be effected with much less solvent than if the reaction mass is crystallized after a water or methanol-water treatment or after complete removal of the phenol by distillation from a respective solvent. For instance, when crystallizing from toluene, the process of the invention requires only 1/6 of the normally needed quantity.

As adjuvants for the separation of the reaction product, there can be used polyethylene glycols of the formula H(—O—CH$_2$—CH$_2$—)$_n$ OH wherein n is 2 to 13, that is, those having a glycerin-like flow behavior. But also other corresponding polypropylene glycols or other polyalkylene glycols can be employed. Special preference, however, is given to triethylene glycol by which a crude yield of more than 90% can be achieved. The attainable crude yields diminish with increasing molecular weight of the polyglycol used. Thus, with a polyethylene glycol of a molecular weight of 200, only about 70% crude yield is obtained.

The stirrability of the reaction mass is preserved by filling up with 15 to 25% glycol, based on the volume of the reaction mass, before distilling the excess phenol. After the phenol has been distilled off, the product can be crystallized from dichloroethane, toluene, a toluene/isopropanol mixture, acetonitrile and other solvents miscible with the polyalkylene glycols used. By subsequent treatment with water, 9,9-bis-(4-hydroxphenyl)-fluorene is obtained as a white crystalline product after drying.

To carry out the process, fluorenone and phenol are charged in to a reaction vessel, e.g. in the molar ratio of 1:6, and β-mercaptopropionic acid is added as catalyst in a quantity of about 0.01 mole per mole of fluorenone used. This mixture is heated to a temperature of 50 to 60° C. While stirring, dry hydrogen chloride gas is introduced in an amount of about 0.3 to 0.45 mole per mole of fluorenone used, continuing to stir for another 2 to 6 hours. Thereafter, the reaction mixture is diluted with about 15 wt % of triethylene glycol, based on the total volume.

Thereafter, at reduced pressure and at 40 and 90° C, the resulting reaction water is distilled off together with the dissolved hydrochloric acid. After a short aqueous head fraction, the excess phenol can now be distilled at 90 to 115° C. The distillation residue remains well stirrable and can easily be taken up in a solvent and crystallized. For this purpose, the residue is, for example, carefully diluted at reflux with 1.5 times the volume of toluene. The suspension obtained is cooled while stirring and crystallization occurs at about 80° C. The product is suction filtered at about 5° C. and washed again with cold toluene. The product isolated is then suspended in water and stirred at 80 to 90° C. After cooling to about 20° C., the fluorene derivative is suction filtered and dried in vacuum at about 110° C.

In this manner, a crude product with a purity of about 96% is obtained in a theoretical yield of more than 90%. By crystallization from a mixture of toluene/isopropanol (9:2) the purity can be increased to 99.6 to 99.9%. This process can be simplified by adding as solvent after the distillation of the phenol and appropriate amount of acetonitrile and after filtering the precipitated crystalline adduct, 9,9-bis-(4-hydroxphenyl)-fluorene can be obtained after drying in vacuum in a purity of 98% without performing a water treatment.

In the following examples, there are described several preferred embodiments to illustrate the invention. However, it is to be understood that the invention is not intended to be limited to the specific embodiments.

EXAMPLE 1

In a 2-liter three-neck flask, 566 g of phenol, 180 g of fluorenone and 0.8 g of β-mercaptopropionic acid were heated to 55° C. with stirring and over 6 hours, about 14 g of HCl gas were introduced slowly. The temperature was maintained and after complete introduction of gas, stirring was continued for about 2 more hours at 55° C., the product being thereafter diluted with 100 ml (112 g) of triethylene glycol. The resulting reaction water was distilled under water jet vacuum together with the hydrochloric acid formed. Then, phenol was distilled under reduced pressure and the liquid distillation residue was allowed to cool to 120° C. while stirring. 800 ml of toluene were then added slowly at reflux with stirring, with the distillation residue dissolving. When this toluene solution was cooled slowly, crystallization occurred below 80° C. The temperature was reduced to 0° C. in an ice bath and the precipitated crystals were filtered and washed again with 400 ml of cold toluene. Then, the separated triethylene glycol-containing product was suspended in 1000 ml of water and heated to 80 to 90° C. with stirring. The temperature was then reduced to about 20° C. and, the precipitated crystals were filtered. After washing twice with 150 ml of water, the resulting 9,9-bis-(4-hydroxyphenyl)- fluorene was dried in vacuum at 110° C. to obtain 308 g of 9,9-bis-(4-hydroxphenyl)-fluorene (88% of the theory) with a purity of 97% (HPLC). By crystallization from toluene : isopropanol 9: 1, the purity increased to 99.8% (HPLC).

Distilled phenol was collected and returned to the process and the toluene obtained as filtrate can also be re-used, but must be purified by distillation after having been used about three times.

EXAMPLE 2

The procedure of Example 1 was used with instead of fresh triethylene glycol, the triethylene glycol-containing distillation residue obtained from Example 1 was added, which is obtained from the mother liquor and contains as yet not isolated fluorene bisphenol, by-products of the condensation reaction, and small amounts of phenol. This residue was admixed with fresh triethylene glycol to 110 ml and added to the reaction mixture before the phenol was distilled off. In this manner, the product still dissolved in the triethylene glycol from the preceding reaction was obtained, and after complete processing as described in Example 1, 322 g of 9,9-bis-(4-hydroxphenyl)-fluorene (92% of the theory) were obtained with a purity of 96% (HPLC). By crystallization from a toluene : isopropanol mixture 9 : 1, the purity was increased to 99.8% (HPLC).

EXAMPLE 3

The procedure of Example 1 was used with instead of triethylene glycol, there were added 100 ml of a polyethylene glycol mixture with an average molecular weight of approximately 200. The yield of isolated product was 245 g (70% of the theory) with a purity of 98.3% (HPLC). By recrystallization from a solvent mixture of toluene : isopropanol (9 : 1), the purity of the product increased to 99.8% (HPLC).

EXAMPLE 4

Into a melt of 180 g of 9-fluorenone (1 mole), 565 g of phenol (6 moles) and 1 g of mercaptopropionic acid, 14 g of hydrogen chloride (0.38 mole) were added over 6 hours at 55° C. and the mixture was stirred for another 2 hours at 55° C. Then, the reaction mixture was diluted with 110 ml of triethylene glycol and the excess phenol was distilled off under reduced pressure. The head runs contained hydrochloric acid and phenol and the main fraction consisted of 99% phenol which was recycled into the next batch. The distillation residue was allowed to cool to 110° C. with stirring, carefully adding 500 ml of acetonitrile and slowing cooling to 0° C. The precipitating white product was filtered and subsequently dried in vacuum to obtain a yield of 280 g of 9,9-bis-(4-hydroxphenyl)-fluorene (80% of the theory) with a purity of 98%. By crystallizing from acetonitrile, the product had a 99.9% pure white crystalline product.

Various modifications of the process of the invention may be made without deporting from the spirit or scope thereof and it is to be understood that the invention is intended to be limited only as defined in the appended claims.

What we claim is:

1. In the production of 9,9-bis-(4-hydroxphenyl)-fluorene by condensation by fluorenone and phenol in a molar ratio of 1:4 to 1:8 at 30 to 90° C. in the presence of gaseous hydrogen chloride and $\beta$-mercapto-propionic acid as catalyst, the improvement comprising mixing the completed reaction mixture with a polyalkylene glycol, distilling excess phenol from the mixture, and mixing the distillation residue with a solvent miscible with the polyalkylene glycol, recovering the crystallized product, suspending the crystallized product in water and heating the suspension to obtain highly pure 9,9-bis-(4-hydroxyphenyl)-fluorene as white crystals.

2. The process of claim 1 wherein the polyethylene glycol has the formula $H-(-O-CH_2-CH_2)_n-OH$ wherein n is an integer from 2 to 13.

3. The process of claim 1 wherein the polyethylene glycol is triethylene glycol.

4. The process of claim 1 wherein the amount of polyethylene glycol used is 15 to 20% by volume of the reaction mixture.

5. A process for the preparation of at least 99% pure 9,9-bis-(4-hydroxyphenyl)-fluorene comprising condensing fluorenone and phenol in a molar ratio of 1:4 to 1:8 at 30 to 90° C. in the presence of gaseous hydrogen chloride and $\beta$-mercapto-propionic acid as catalyst, mixing the completed reaction mixture with a polyethylene glycol, distilling excess phenol from the mixture, admixing the distillation residue with acetonitrile to form an adduct, filtering the mixture to recover the adduct and drying the adduct in vacuum to obtain 9,9-bis-(4-hydroxphenyl)-fluorene.

* * * * *